United States Patent
Kennedy et al.

(10) Patent No.: US 7,263,889 B2
(45) Date of Patent: Sep. 4, 2007

(54) NON-DESTRUCTIVE STRINGER INSPECTION APPARATUS AND METHOD

(75) Inventors: James C. Kennedy, Renton, WA (US); Dennis P. Sarr, Kent, WA (US); Michael R. Chapman, Federal Way, WA (US); Michael D. Fogarty, Auburn, WA (US); Martin L. Freet, Federal Way, WA (US); Gary E. Georgeson, Federal Way, WA (US); Ronald E. VonWahlde, Puyallup, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/689,245

(22) Filed: Mar. 21, 2007

(65) Prior Publication Data

US 2007/0151375 A1    Jul. 5, 2007

Related U.S. Application Data

(62) Division of application No. 11/041,499, filed on Jan. 24, 2005, now Pat. No. 7,249,512.

(51) Int. Cl.
*G01N 29/24* (2006.01)
(52) U.S. Cl. .......................... 73/620; 73/635; 73/866.5
(58) Field of Classification Search ............... 73/618, 73/620, 635, 866.5
See application file for complete search history.

(56) References Cited

U.S. PATENT DOCUMENTS

| | | | |
|---|---|---|---|
| 4,010,636 A | 3/1977 | Clark et al. | |
| 4,117,733 A | 10/1978 | Gugel | |
| 4,167,880 A | 9/1979 | George | |
| 4,311,052 A | 1/1982 | Jeffras et al. | |
| 4,399,703 A | 8/1983 | Matzuk | |
| 4,466,286 A | 8/1984 | Berbeé et al. | |
| 4,612,808 A | 9/1986 | McKirdy et al. | |
| 4,807,476 A | 2/1989 | Cook et al. | |

(Continued)

FOREIGN PATENT DOCUMENTS

EP    1 193 491 A2    4/2002

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—John E. Chapman
(74) *Attorney, Agent, or Firm*—Alston & Bird LLP

(57) ABSTRACT

A hat stringer inspection device permits continuous inspection of hat stringers as one or more probes are moved along the length of the hat stringer. Probes may be magnetically coupled to opposing surfaces of the structure, including, for example, where one of the probes is positioned inside the hat stringer and the probes are magnetically coupled across the surface of the hat stringer. The device may be autonomous with a feedback-controlled motor to drive the inspection device along the hat stringer. Magnetic coupling is also used to re-orient the position and/or alignment of the probes with respect to changes in the hat stringer or shapes, sizes, and configurations of hat stingers.

20 Claims, 19 Drawing Sheets

U.S. PATENT DOCUMENTS

| | | | |
|---|---|---|---|
| 4,848,159 | A | 7/1989 | Kennedy et al. |
| 5,062,301 | A | 11/1991 | Aleshin et al. |
| 5,593,633 | A | 1/1997 | Dull et al. |
| 5,902,935 | A | 5/1999 | Georgeson et al. |
| 6,167,110 | A | 12/2000 | Possin et al. |
| 6,484,583 | B1 | 11/2002 | Chennell et al. |
| 6,507,635 | B2 | 1/2003 | Birdwell et al. |
| 6,658,939 | B2 | 12/2003 | Georgeson et al. |
| 6,711,235 | B2 | 3/2004 | Galish et al. |
| 6,722,202 | B1 | 4/2004 | Kennedy et al. |
| 6,748,791 | B1 | 6/2004 | Georgeson et al. |
| 2003/0154801 | A1 | 8/2003 | Georgeson |
| 2003/0210027 | A1 | 11/2003 | Pedigo et al. |
| 2004/0037393 | A1 | 2/2004 | Birdwell et al. |
| 2004/0103721 | A1 | 6/2004 | Georgeson |

OTHER PUBLICATIONS

*Inspection of In-Service Composite-Honeycomb Structures*, Aerospace Application Note, Rev.: 2002-01, R/D Tech.

*Probe Catalog 2003-2004*, Thru-Transmission Ultrasonics, NDT Engineering Corporation, R/D Tech Company, pp. 1-11.

*Air-Coupled Ultrasonic Inspection*, http://www.qmi-inc.com/AIRSCAN.htm, Aug. 19, 2004, 3 pages.

U.S. Appl. No. 10/734,452, filed Dec. 12, 2003, In re: Bossi et al., entitled*Ultrasonic Inspection Device for Inspecting Components at Preset Angles*.

U.S. Appl. No. 10/752,890, filed Jan. 7, 2004, In re: Bossi et al., entitled*Non-Destructive Inspection Device for Inspecting Limited-Access Features of a Structure*.

U.S. Appl. No. 10/943,088 filed Sep. 16, 2004, In re: Georgeson et al., entitled *Magnetically Attracted Inspecting Apparatus and method Using a Ball Bearing*.

U.S. Appl. No. 10/943,068, filed Sep. 16, 2004; In re: Georgeson et al., entitled*Apparatus and Method for Area Limited-Access Through Transmission Ultrasonic Inspection*.

U.S. Appl. No. 10/943,135, filed Sep. 16, 2004; In re: Georgeson et al., entitled *Magnetically Attracted Inspecting Apparatus and Method Using a Fluid Bearing*.

U.S. Appl. No. 10/943,170, filed Sep. 16, 2004; In re: Georgeson et al., entitled*Alignment Compensator for Magnetically Attracted Inspecting Apparatus and Method*.

U.S. Appl. No. 10/943,045; filed Sep. 16, 2004; In re: Wright et al., entitled*End Effector Inspection Apparatus and Method*.

*Air-Coupled Ultrasonic Measurements of Adhesively Bonded Multi-Layer Structures*, D. W. Schindel; Ultrasonics, IPC Science and Technology Press Ltd., vol. 37, No. 3, Mar. 1999, pp. 185-200.

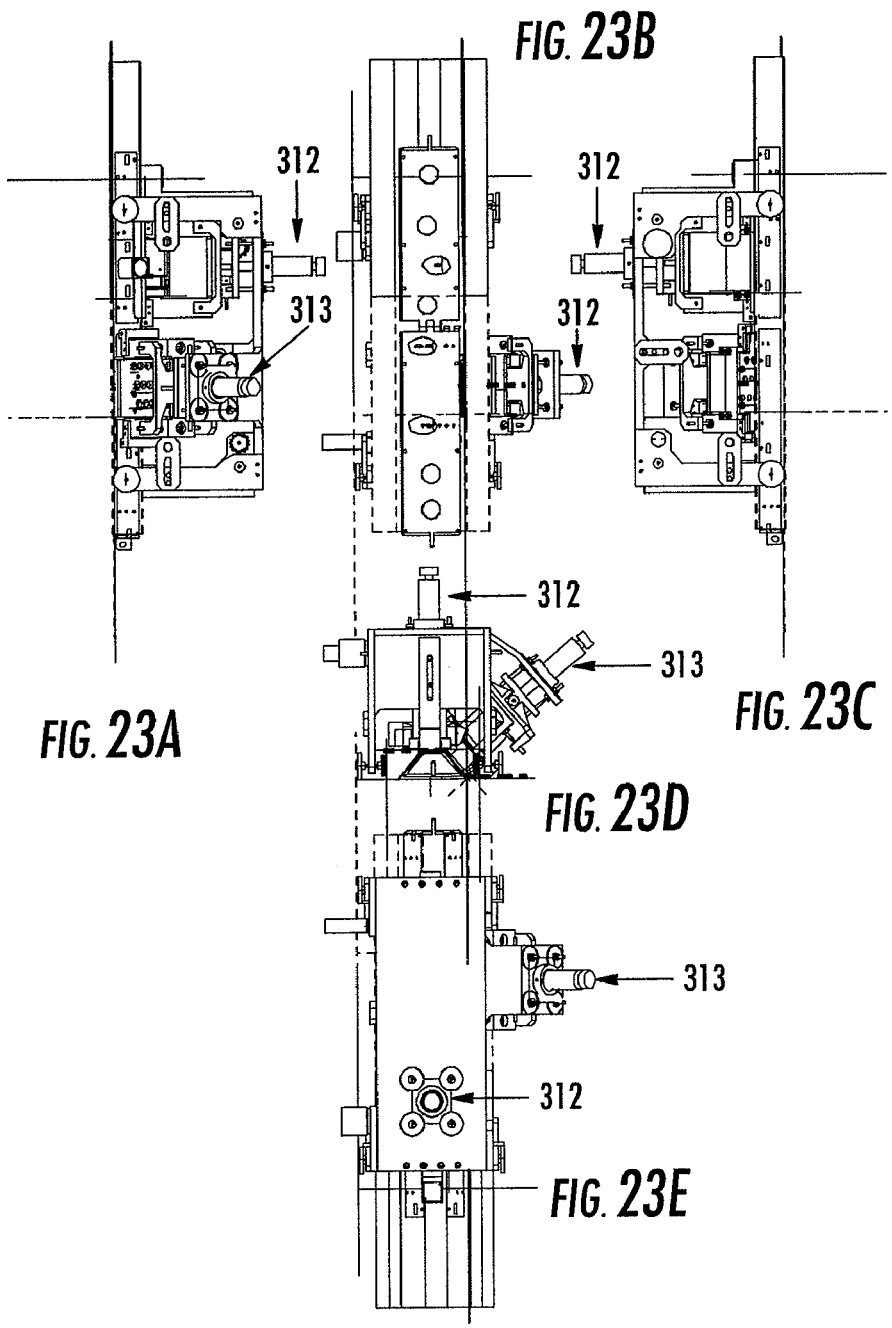

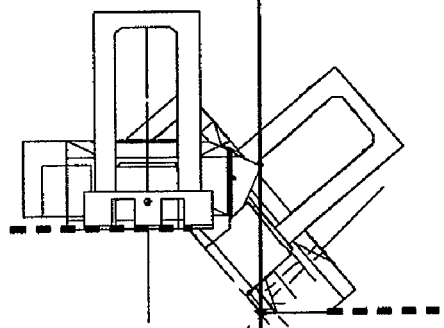
FIG. 23F
FIG. 23G
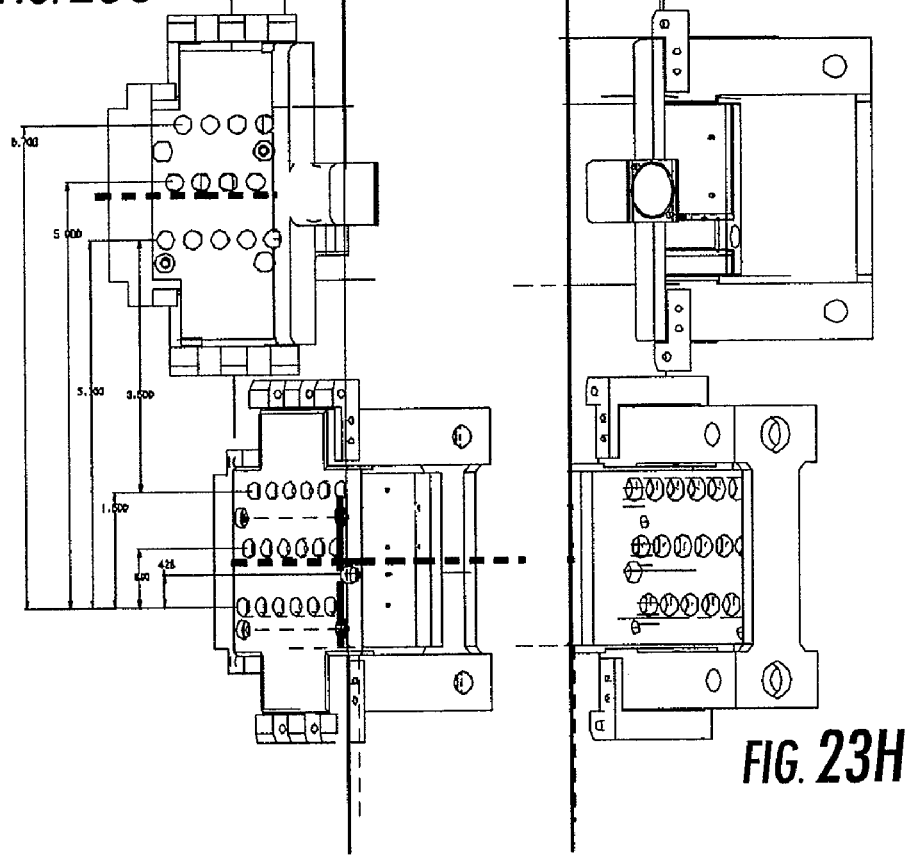
FIG. 23H

SECTION A-A

SECTION B-B

SECTION C-C

SECTION D-D

SECTION E-E

NON-DESTRUCTIVE STRINGER INSPECTION APPARATUS AND METHOD

CROSS-REFERENCE TO RELATED APPLICATIONS

This application claims priority from and is a divisional of U.S. application Ser. No. 11/041,499, filed Jan. 24, 2005, now U.S. Pat. No. 7,249,512 the contents of which is hereby incorporated by reference herein in its entirety. The contents of U.S. Pat. No. 6,722,202 and application Ser. No. 10/752,890, entitled "Non-Destructive Inspection Device for Inspection Limited-Access Features of a Structure," filed Jan. 7, 2004; application Ser. No. 10/943,135 entitled "Magnetically Attracted Inspecting Apparatus and Method Using a Fluid Bearing," filed Sep. 16, 2004; application Ser. No. 10/943,088, entitled "Magnetically Attracted Inspecting Apparatus and Method Using a Ball Bearing," filed Sep. 16, 2004; and application Ser. No. 10/943,170, entitled "Alignment Compensator for Magnetically Attracted Inspecting Apparatus and Method," filed Sep. 16, 2004, are hereby incorporated by reference herein in their entirety.

FIELD OF THE INVENTION

The present invention relates generally to an apparatus and method for inspecting a structure and, more particularly, to an apparatus and method for non-destructive inspection of limited-access features of a structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies, such as hat stringers or hat stiffeners made from carbon fiber reinforced and graphite epoxy (Gr/Ep) materials and co-cured or co-bonded hat stringers. In this regard, composite structures are commonly used throughout the aircraft industry because of the engineering qualities, design flexibility and low weight, such as the stiffness-to-weight ratio. As such, it is frequently desirable to inspect composite structures to identify any flaws, such as cracks, voids or porosity, which could adversely affect the performance of the composite structure.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bond-lines of the structure. High resolution inspection of aircraft structure are commonly performed using semi-automated ultrasonic testing (UT) to provide a plan view image of the part or structure under inspection. For example, solid laminates may be inspected using one-sided pulse echo ultrasonic (PEU) testing and composite sandwich structures may be inspected using two-sided through-transmission ultrasonic (TTU) testing. In pulse echo ultrasonic (PEU) testing, ultrasonic sensors, such as ultrasonic transducers, are positioned adjacent to or near one surface of the structure to be inspected. For example, the PEU transducer transmits an ultrasonic signal into the structure under inspection and receives the reflection of the ultrasonic signal from the structure. In through-transmission ultrasonic inspection, paired ultrasonic sensors such as transducers, or transducer and a receiver pairings, are positioned facing the other but contacting opposite sides of the structure. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display. A data acquisition board and data handling software may be used for collection and display of inspection data, such as displaying the data on a computer monitor as an image representation of the structure under inspection, such as a hat stringer, supplemented with corresponding color and/or graphical data of the inspection to permit examination by a qualified inspector.

Non-destructive inspection may be performed manually by technicians who typically move an appropriate sensor over the structure. Manual scanning requires a trained technician to move the sensor over all portions of the structure needing inspection. Manual scanning typically involves the technician repeatedly moving a sensor side-to-side in one direction while simultaneously indexing the sensor in another direction. In addition, because sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have also been developed. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician.

Automated inspection systems have also been developed. For example, the Automated Ultrasonic Scanning System (AUSS®) system is a complex mechanical scanning system that may employ through-transmission ultrasonic inspection. An AUSS system can also perform pulse echo inspections, and simultaneous dual frequency inspections. The AUSS system has robotically controlled probe arms that may be positioned, for example, for TTU inspection proximate the opposed surfaces of the structure undergoing inspection with one probe arm moving an ultrasonic transmitter along one surface of the structure, and the other probe arm correspondingly moving an ultrasonic receiver along the opposed surface of the structure. To maintain the ultrasonic transmitter and receiver in proper alignment and spacing with one another and with the structure undergoing inspection, a conventional automated inspection system may have a complex positioning system that provides motion control in numerous axes, such as the AUSS-X system which has motion control in ten axes. Automated inspection systems, and like robotics, however, can be prohibitively expensive. Further, orienting and spacing sensors with respect to the structure, and with respect to one another for TTU inspection, may be especially difficult in conjunction with structures with non-planar shapes, such as the inspection of curved structures and hat stringers. Also, conventional automated scanning systems, such as the AUSS-X system, may require access to both sides of a structure which, at least in some circumstances, will be problematic, if not impossible, particularly for very large or small structures. Furthermore, scanning systems inspect limited areas up to a few meters square.

Accessibility to the structure requiring inspection and to particular features is also an important consideration. Access may be so limited that manual inspection or automated inspection is not possible. For example, the inside of a hat stringer of the fuselage of an aircraft has limited access for inspection, especially far from an end.

SUMMARY OF THE INVENTION

An apparatus for inspecting a structure, such as a hat stringer, includes autonomous crawlers coupled to the fuselage to inspect the hat stringers using a feedback-controlled motor to drive the inspection device. The present system is particularly adapted for inspecting composite hat stringers.

Magnetic coupling holds the inspection device on the structure under inspection on opposite sides for through transmission inspection. The first probe of the inspection device rides along the outside of the hat stringer while the second probe rides below the hat stringer or inside the hat stringer. The magnetic coupling along with the configuration of the inspection device keep inspection sensors, such as ultrasonic transducers or x-ray sources and detectors, are aligned to inspect the hat stringer as the inspection device moves along the length of the hat stringer. The magnetic coupling keeps the transducers coupled and in physical contact with the surfaces of the structure. Keeping the transducers coupled to the structure is important to ensure reliable inspection, such as to provide for strong and consistent signal transmission. The design of the inspection device also permits accurate position measurement or sensing along the length of the structure by using an encoder.

Embodiments of the present invention refine general features and functionality of the Remote Access Bondline Inspection Tool (RABIT) as described in U.S. patent application Ser. No. 10/752,890, filed Jan. 7, 2004, for inspecting hat stringers.

The preferred design accommodates variations of different hat stringer design shapes and sizes and part thickness changes, such as axial part thickness variance. For example, a central section and side sections of an interior probe may be arranged to permit the side sections to move to match the angle of the sides of the hat stringer. The probe might be self-adjusting using a spring loading or more sophisticated adjustment means like adjustment slots or jackscrews. Transducers oriented to inspect the corners of the hat stringer will remain aligned with the corners by telescoping a middle section as the hat stringer increases in width. Selection of transducers depends on the type of material and its thickness. Higher frequency transducers usually are used for thinner hat stringer thicknesses.

BRIEF DESCRIPTION OF THE DRAWING(S)

Figure 8:
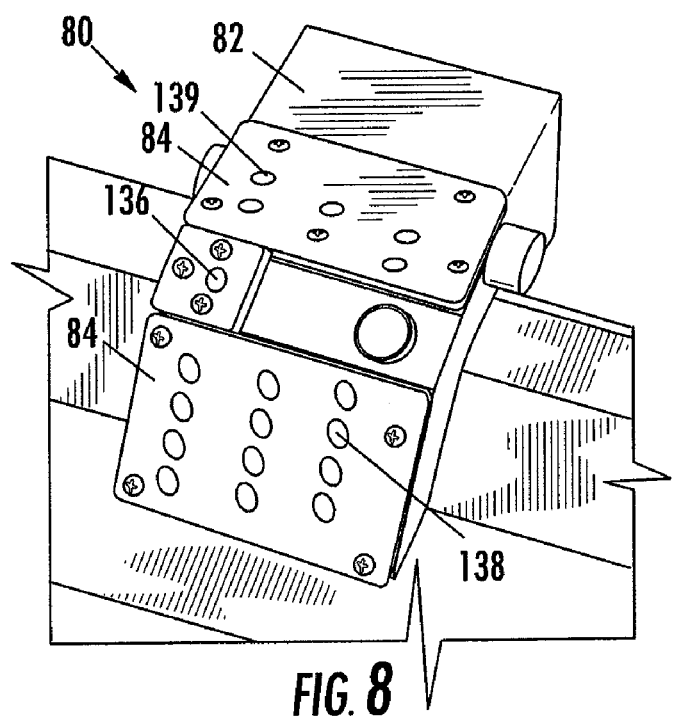
FIG. 8 is a perspective view of yet another inspection probe.
Figure 9:
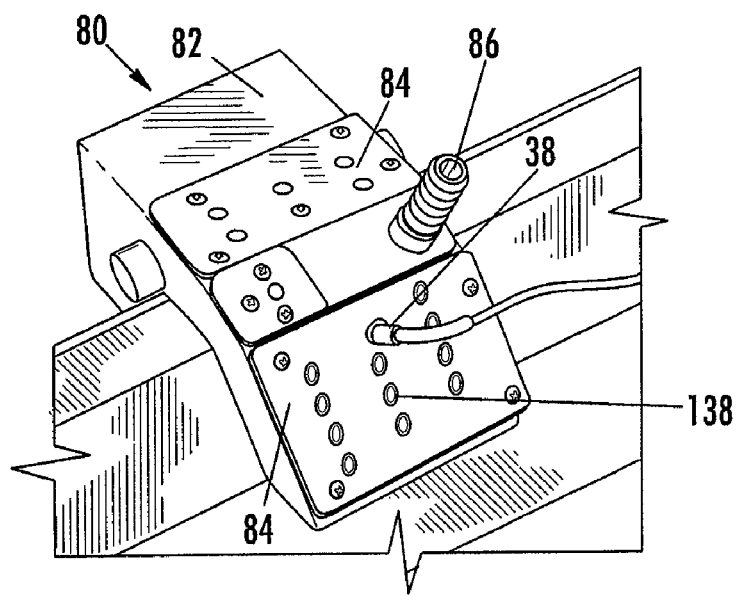
Figure 10:
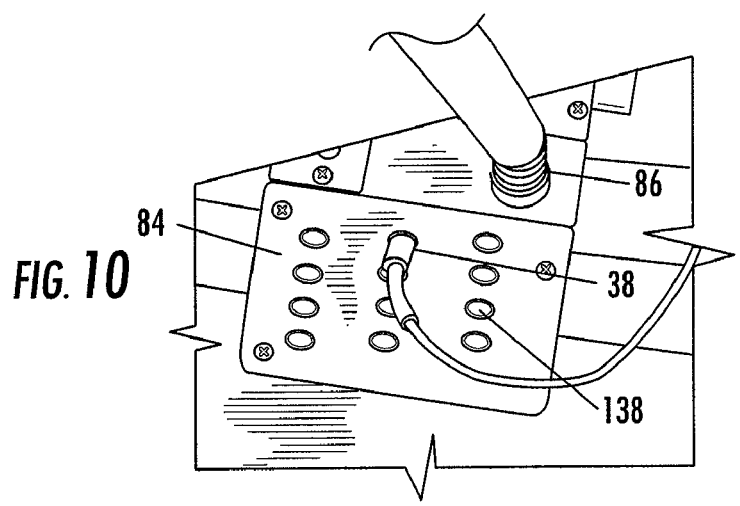

FIGS. 9, 10, 11, and 12 are perspective views of the inspection probe of FIG. 8.

Figure 13:
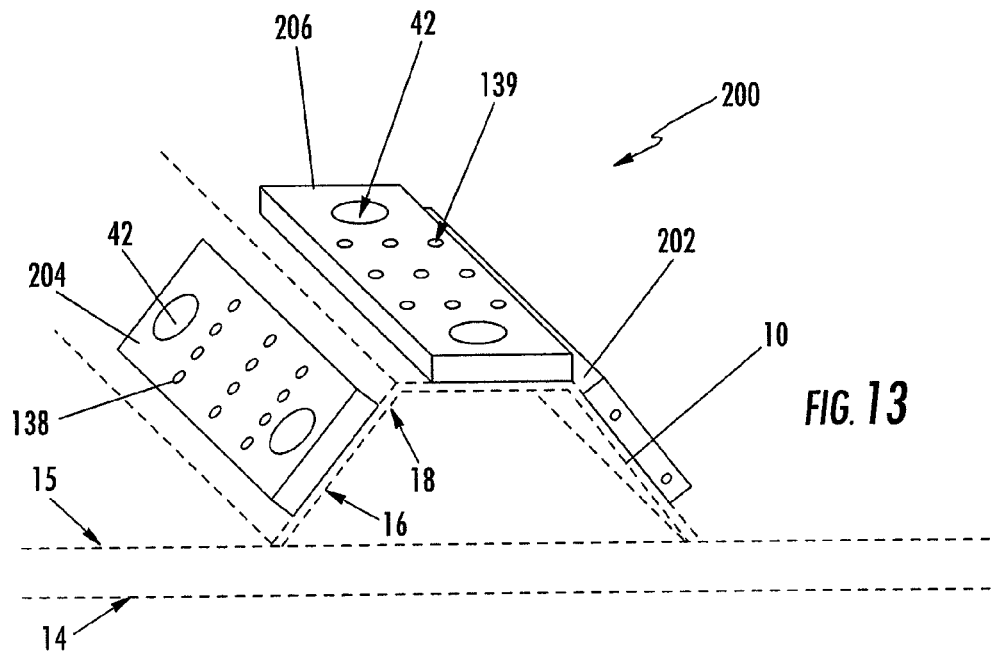
Figure 14:
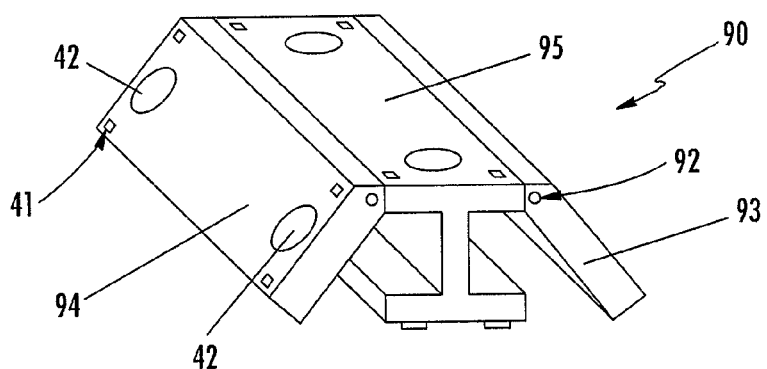
Figure 15:
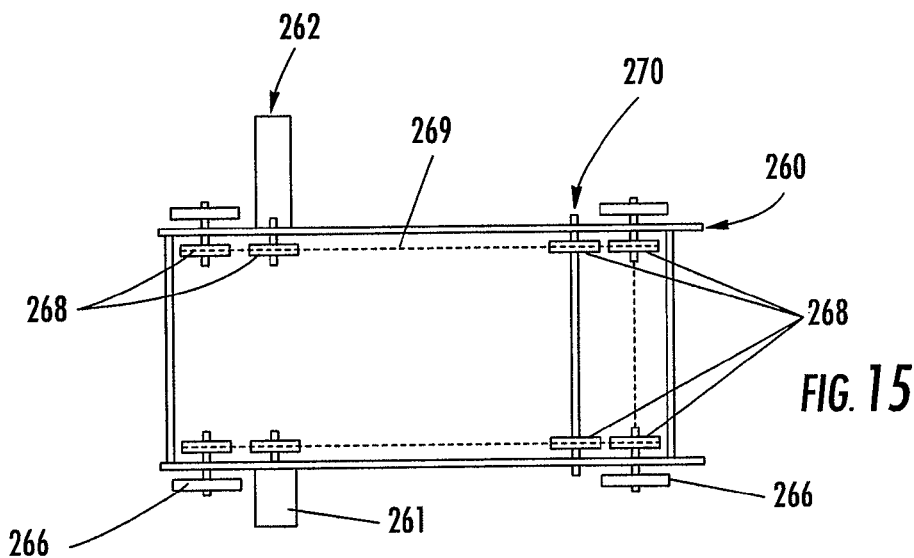

FIGS. 13, 14, and 15 are perspective views of yet other inspection probes.

Figure 16:
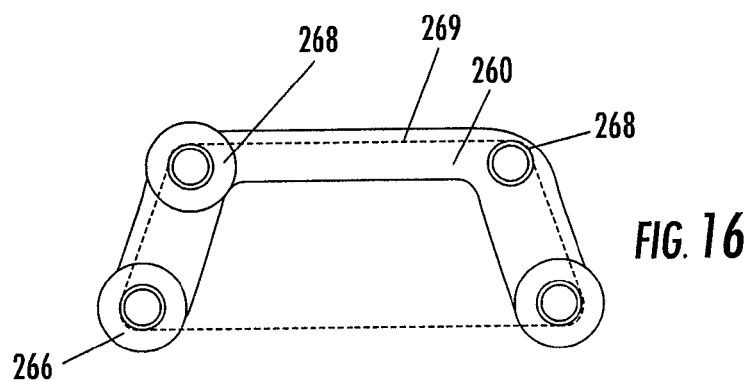
Figure 17:
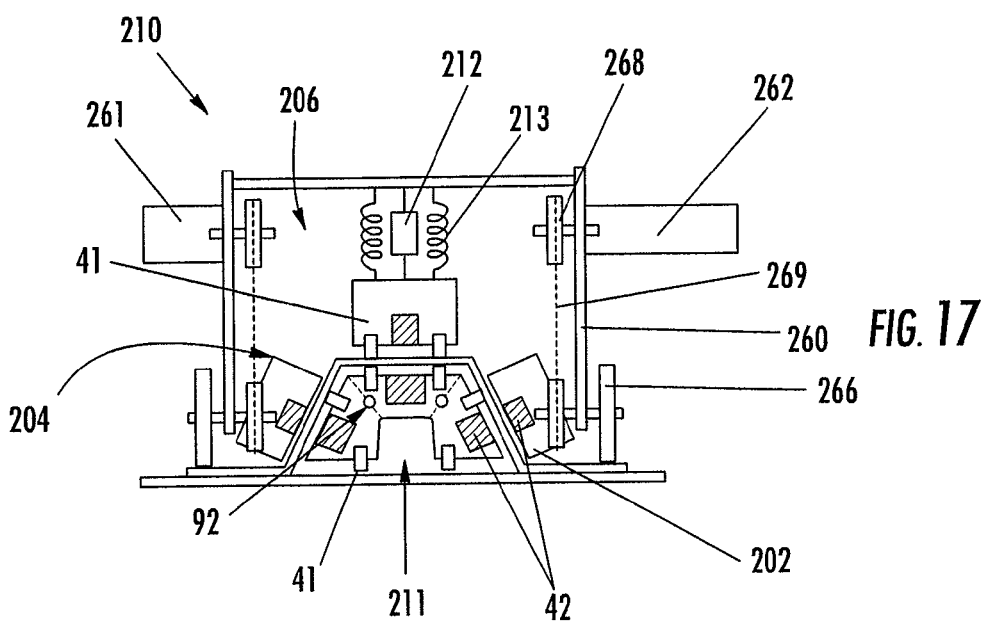

FIGS. 16 and 17, respectively, are side elevation and cross-sectional views of the probe of FIG. 15.

Figure 18:
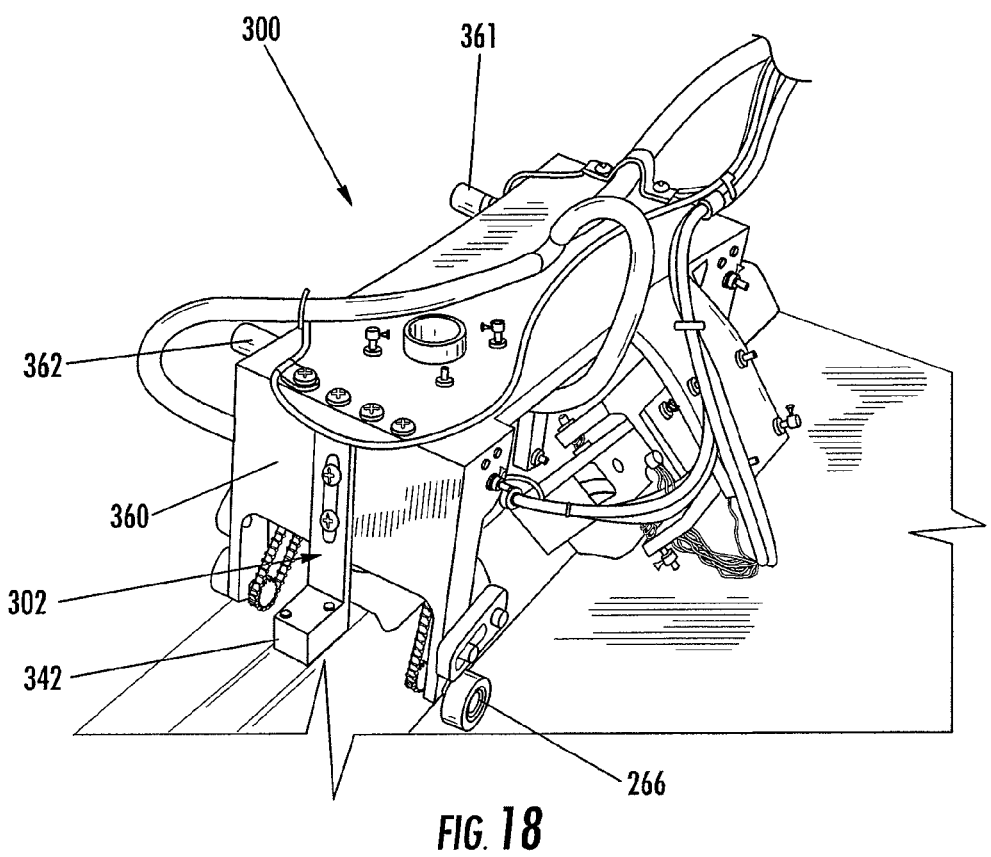
Figure 19:
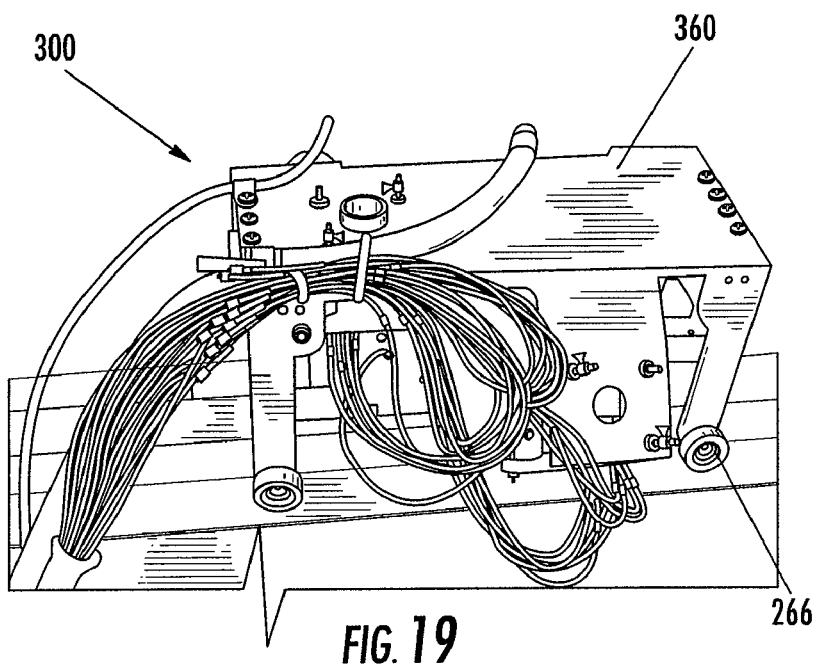
Figure 20:
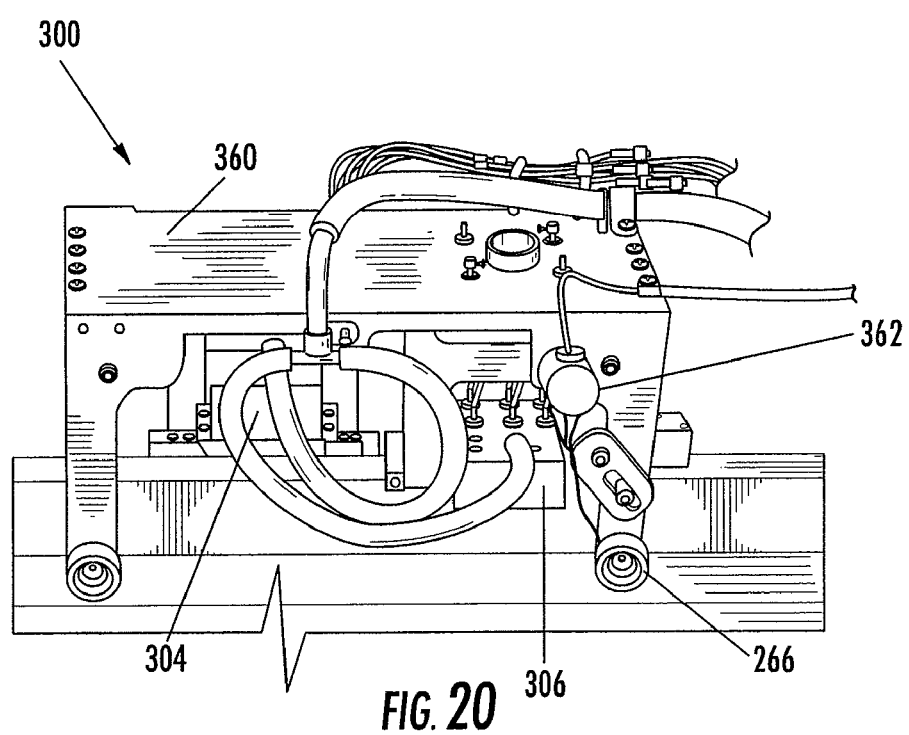
Figure 21:
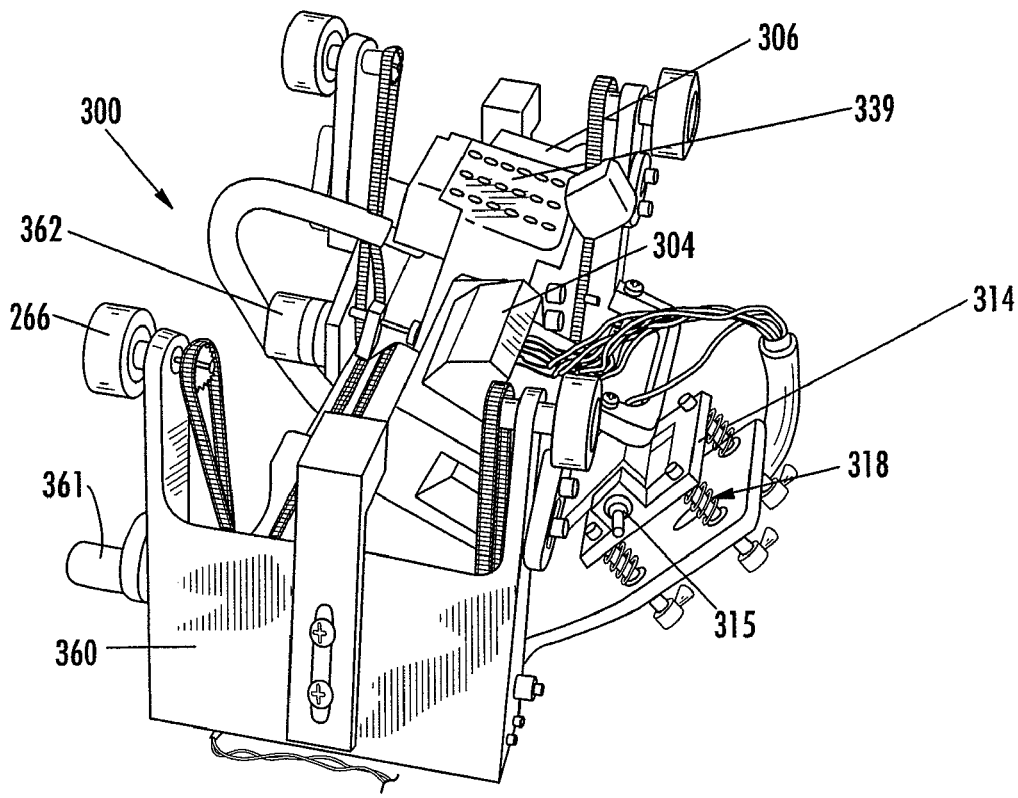
Figure 22:
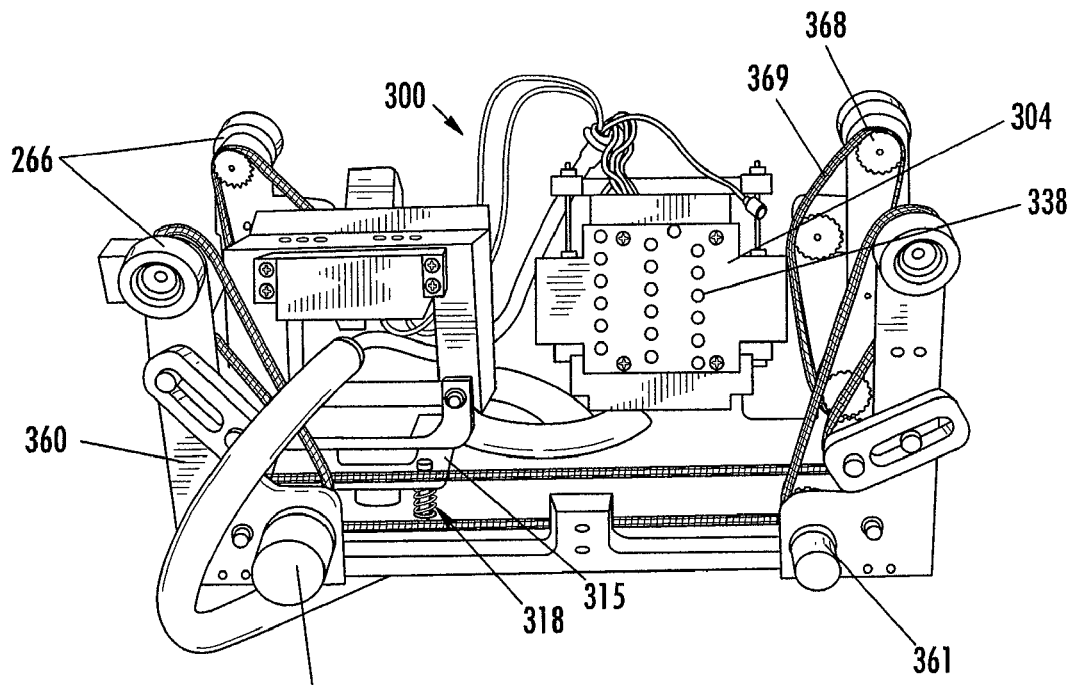

FIG. 18 is a perspective view of yet another inspection probe.

FIGS. 19, 20, 21, and 22 are perspective views of the probe of FIG. 18.

FIG. 23A is a right side elevation view of yet another probe.

FIG. 23B is a bottom plan view of the probe of FIG. 23A.

FIG. 23C is a left side elevation view of the probe of FIG. 23A.

FIG. 23D is a front elevation view of the probe of FIG. 23A.

FIG. 23E is a top plan view of the probe of FIG. 23A.

FIG. 23F is a partial front elevation view of the probe of FIG. 23A.

FIG. 23G is a partial bottom plan view of the probe of FIG. 23A.

FIG. 23H is a partial right side elevation view of the probe of FIG. 23A.

Figure 24:
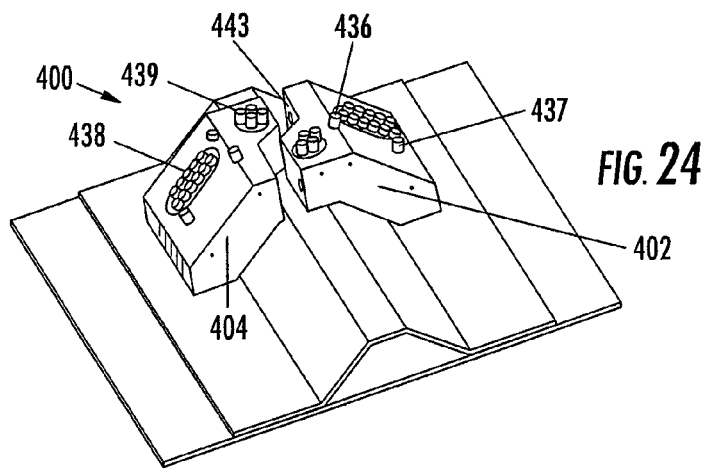

FIG. 24 is a perspective view of yet another inspection probe.

Figure 25:
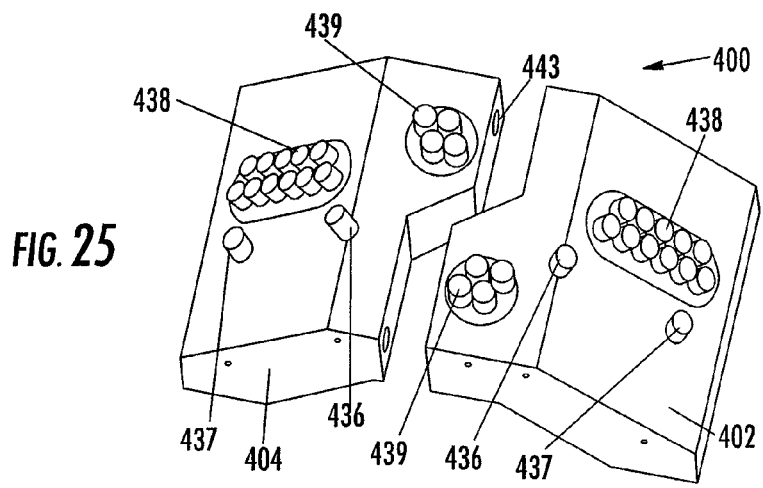
Figure 26:
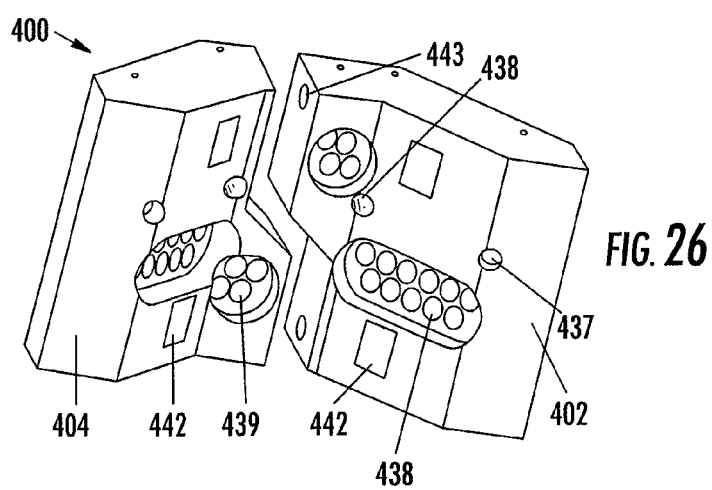

FIGS. 25 and 26 are perspective views of the probe of FIG. 24.

Figure 27:
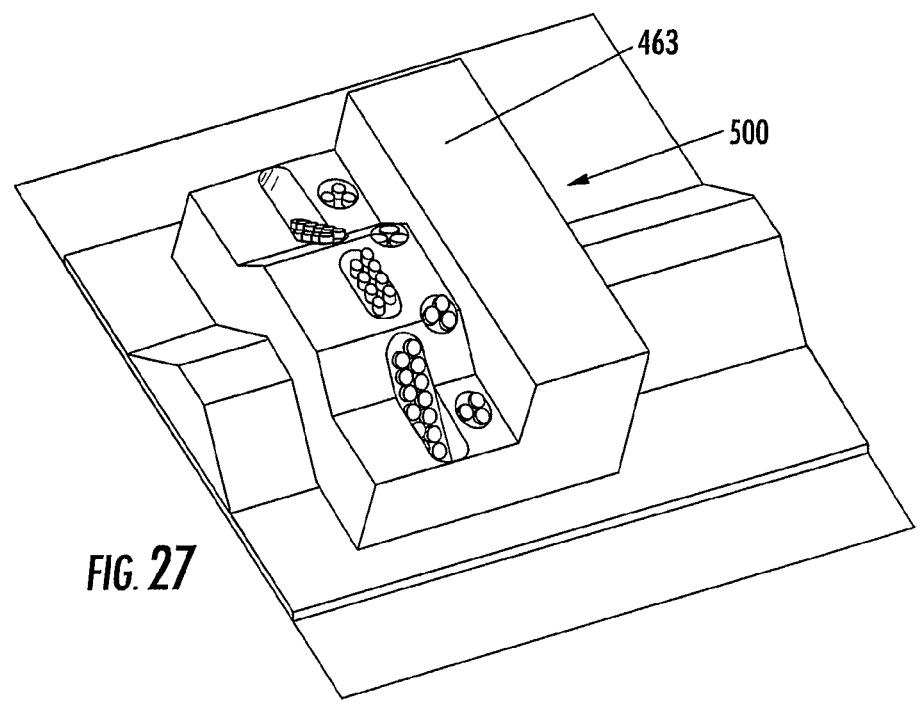

FIG. 27 is a perspective view of yet another inspection probe.

Figure 28:
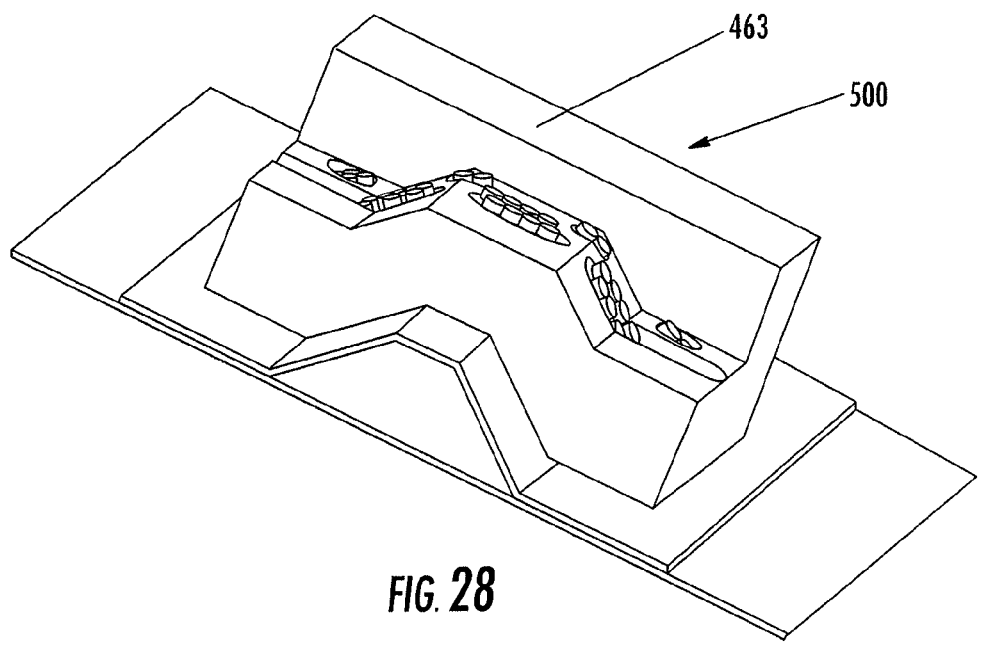
Figure 29:
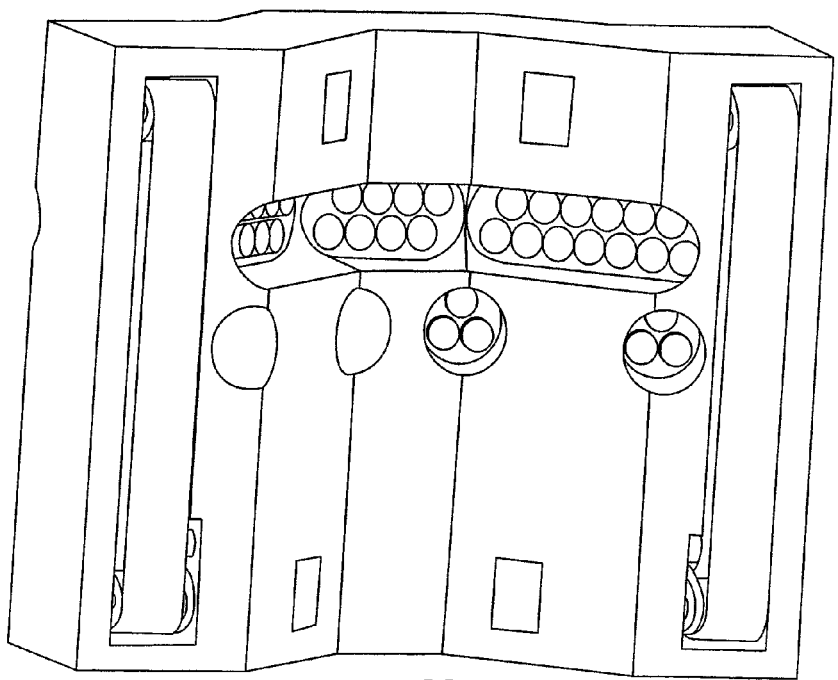
Figure 30:
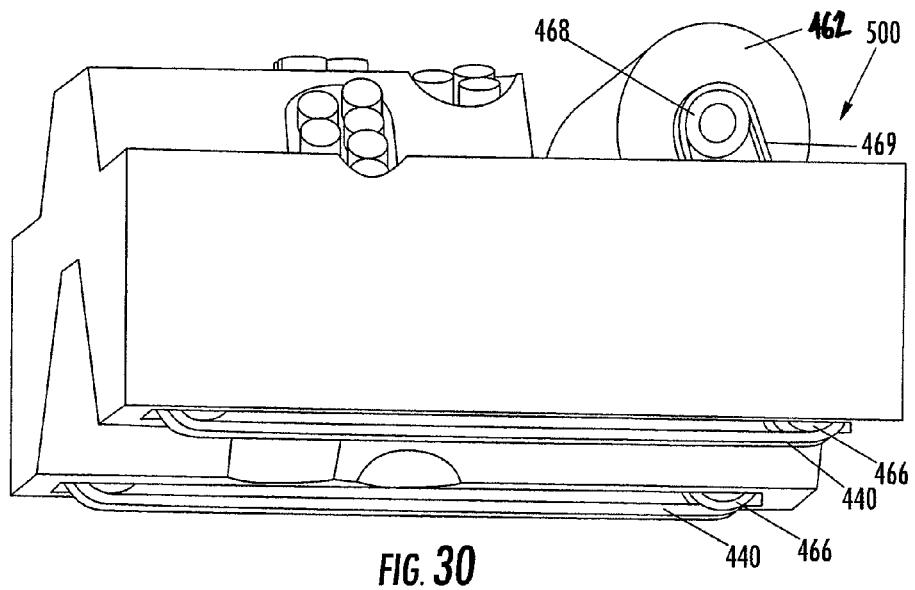

FIGS. 28, 29, and 30 are perspective views of the probe of FIG. 27.

Figure 31A:
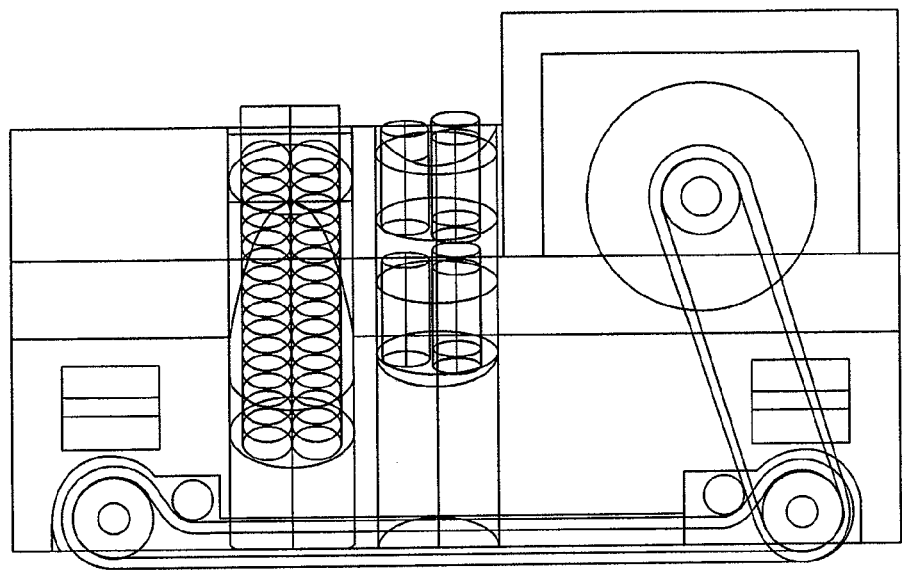

FIG. 31A is a cross-sectional schematic diagram of the probe of FIG. 27.

Figure 31B:
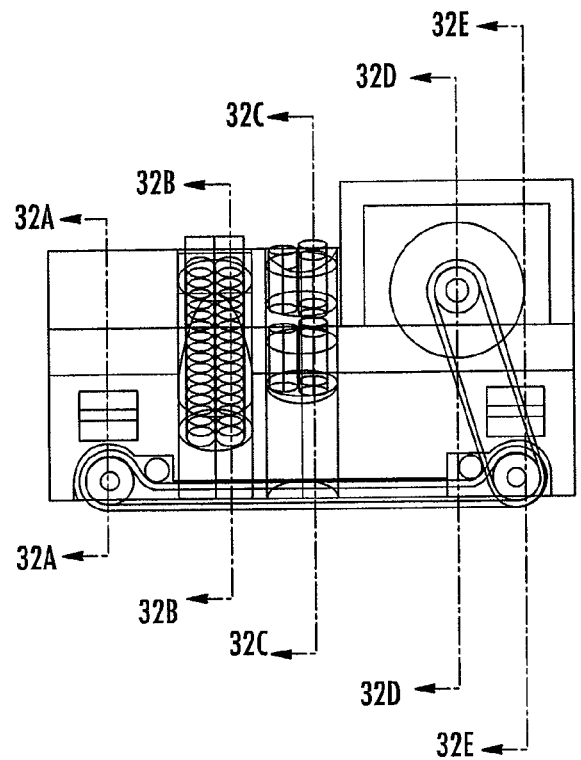

FIG. 31B is a cross-sectional plan view of the probe of FIG. 27.

Figure 32A:
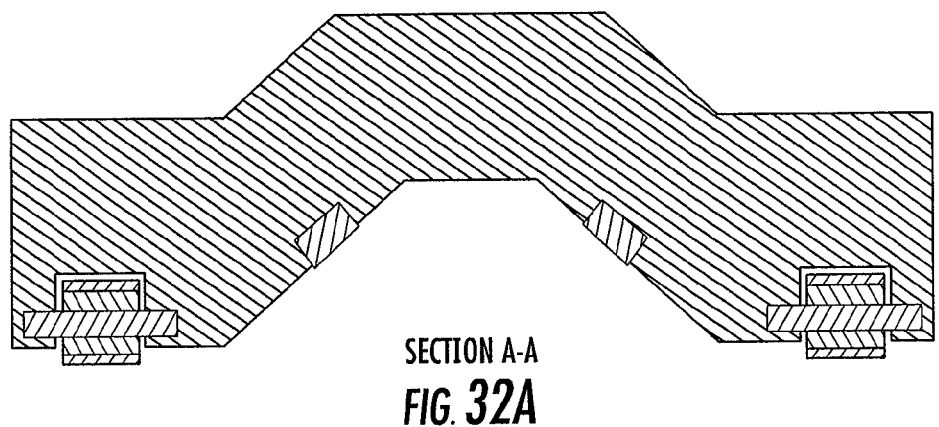

FIG. 32A is a cross-sectional schematic diagram of a section of the probe of FIG. 27 as indicated by A-A in FIG.31 B.

Figure 32B:
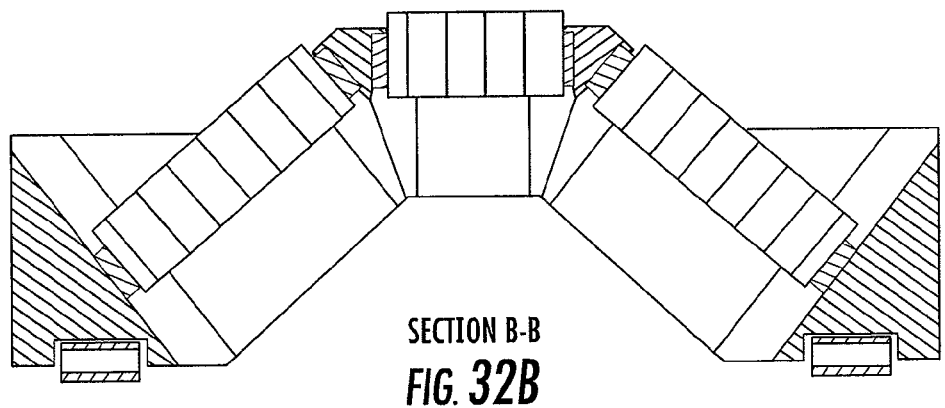

FIG. 32B is a cross-sectional schematic diagram of a section of the probe of FIG. 27 as indicated by B-B in FIG.31B.

Figure 32C:
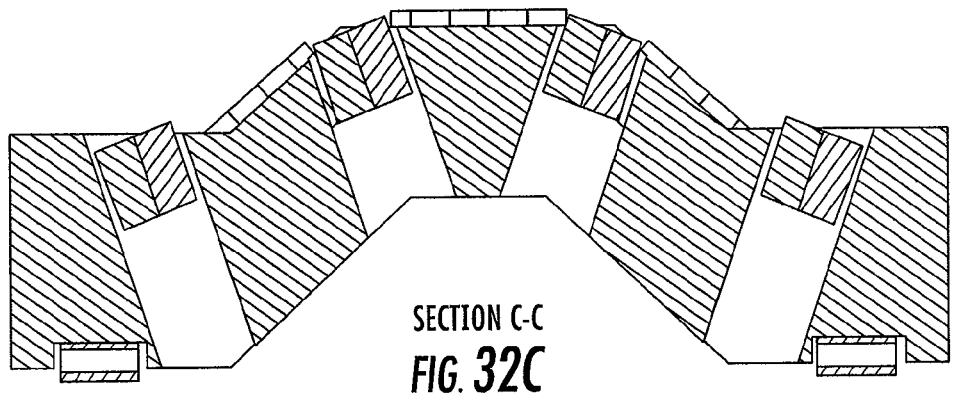

FIG. 32C is a cross-sectional schematic diagram of a section of the probe of FIG. 27 as indicated by C-C in FIG. 31B.

Figure 32D:
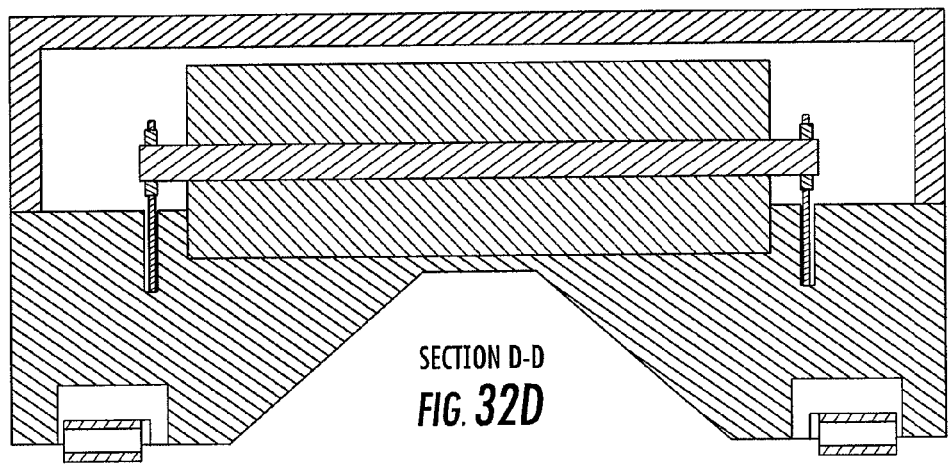

FIG. 32D is a cross-sectional schematic diagram of a section of the probe of FIG. 27 as indicated D-D in FIG. 31B.

Figure 32E:
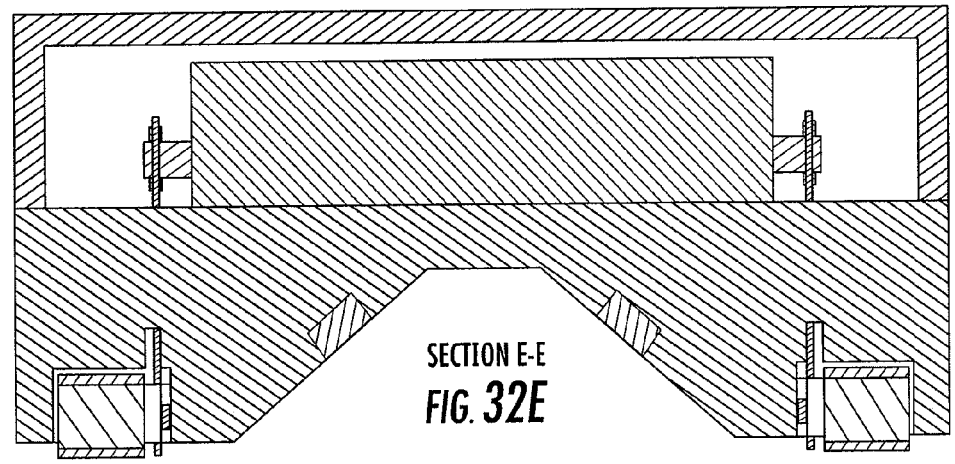

FIG. 32E is a cross-sectional schematic diagram of a section of the probe of FIG. 27 as indicated E-E in FIG. 31B.

DETAILED DESCRIPTION

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

Embodiments of non-destructive stringer inspection apparatus and methods of the present invention are described with respect to hat stringers, especially composite hat stringers for an aircraft fuselage. However, the apparatus and methods may also be used for similar applications which require non-destructive inspection, including other composite structures with difficult-to-inspect geometric configurations and/or remote locations. Embodiments of hat stringer inspection apparatus and methods may include magnetically coupled probes as described in co-pending applications Ser. Nos. 10/943,088; 10/943,135; 10/752,890; or 10/943,170.

Inspection devices can inspect a variety of structures formed of various materials. For devices which transmit magnetic fields through the structure, however, the structure under inspection is preferably non-magnetic, that is, the structure preferably has no magnetic permeability. Such structures include composites such as carbon fiber or graphite reinforced epoxy (Gr/Ep) and non-ferromagnetic metals (e.g. aluminum alloy, titanium alloy, or aluminum or titanium hybrid laminates such as GLARE or Ti/Gr). The surfaces and intermediate septums which collectively define the test article are non-magnetic to allow magnetic coupling between the probes.

Inspecting hat stringers normally requires a one-sided inspection technique, such as pulse echo ultrasonic (PEU) inspection. However, the shapes of hat stringers complicate the inspection. The hat stringer inspection device can perform pulse echo inspection or through transmission ultrasonic (TTU) inspection.

Inspection sensors of a probe may be strategically placed and oriented, such as aiming transducers at the corners or edges of the hat stiffener, to ensure full inspection of the entire hat stringer. Support structures for inspection sensors, also referred to as transducer holders, may be fabricated for specific placement and orientation of inspection sensors corresponding to the intended shapes and sizes of hat stringers. For example, the first inspection probe 80 with transducer holders 84 shown in FIGS. 8-12 may be used for handheld pulse echo (PE) inspection using twelve inspection sensors 38 on one side of the hat stringer and six inspection sensors 38 on the top section of the hat stringer. Inspection sensors located near the intersecting corner of the hat stringer between the top section and one of the sides may be oriented to inspect the corner. Alternatively, or in addition, inspection sensors may be included between the side and top to inspect a corner of the hat stringer. An inspection device using the transducer holders 84 shown in FIGS. 8-12 would require scanning the hat stringer once along each side of the hat stringer. Other embodiments may be configured to scan both sides and the top section of a hat stringer to permit single-pass inspection.

Three types of inspection probes are provided. A fixed orientation probe includes a housing that supports any of inspection sensors, contact members, and magnetic coupling devices such that the inspection probe functions as a single, integrated device. A segmented probe decouples the housing that supports any contact members and/or magnetic coupling devices from transducer holders that support the inspection sensors such that the probe is capable of re-orienting the transducer holders and, thereby, any inspection sensors with the shape and structure of the hat stringer under inspection. A partially fixed orientation probe may include hinged sections which permit limited re-orientation of the inspection probe to permit better alignment of inspection sensors or positioning of magnetic coupling devices and/or contact members. These three variations of inspections probes may be used in different combinations depending on the particular circumstances of inspection.

Figure 1:
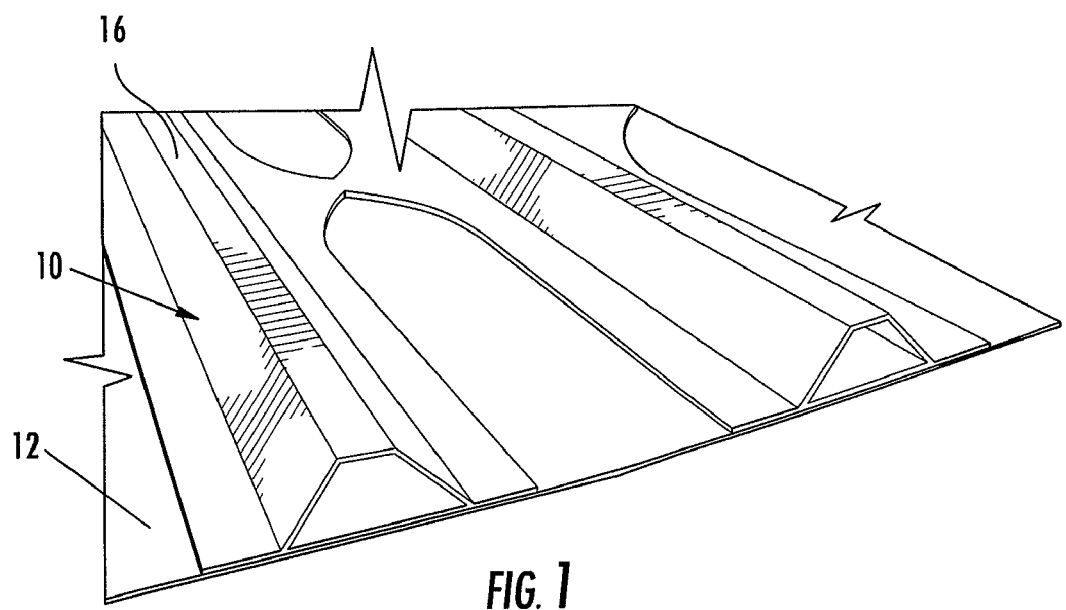
FIG. 1 is a perspective view of a structure with two hat stringers.
Figure 2:
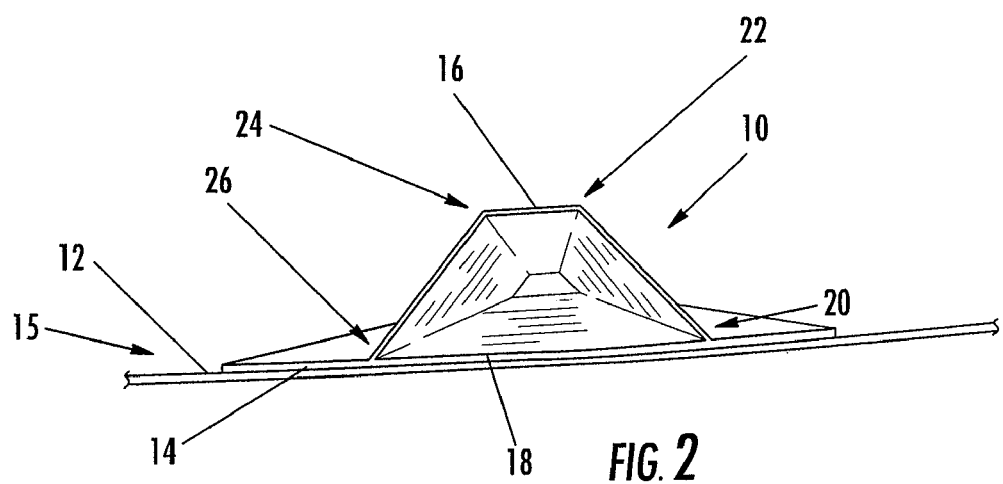
FIG. 2 is an isometric view of a hat stringer.

FIG. 1 is a perspective view of a structure with two hat stringers. Their structure includes a skin 12 to which individual or connected hat stringers 10 may be attached to stiffen for the overall structure. In FIG. 2, the hat stringer has an outside surface 16 and an inside surface 18. The skin 12 has an upper surface 15 and a lower surface 14. The hat stringer 10 is a trapezoidal structure and is affixed to the skin 12 at corners or edges 20, 26. The hat stringer 10 has corners or edges 22, 24 that are lifted off of the skin.

Figure 3:
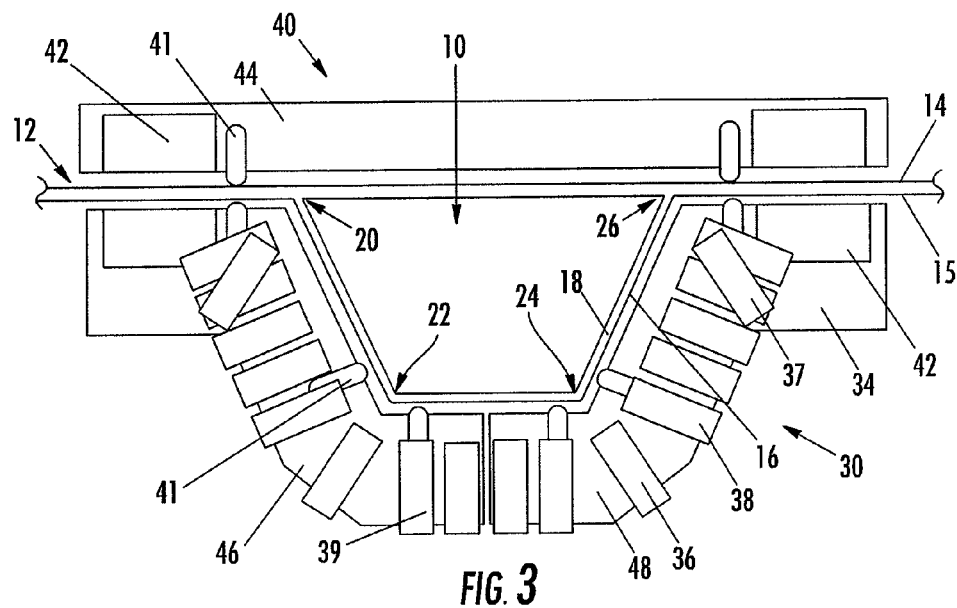
FIG. 3 is a cross-sectional schematic diagram of an inspection apparatus of the present invention for inspecting a hat stringer.
Figure 4:
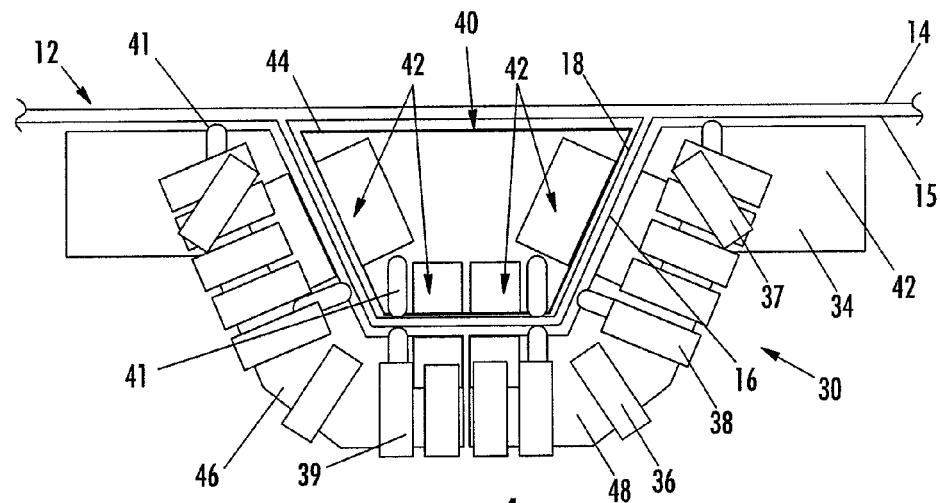
FIG. 4 is a cross-sectional schematic diagram of another embodiment of the inspection apparatus.

If access is available under the hat stringer at the exterior surface of the fuselage, magnetic coupling through the fuselage wall will hold the first probe on the hat stringer and the second probe against the interior surface of the fuselage, as shown in FIG. 3. If access is not available to the exterior surface of the fuselage and/or the hat stringer has an open end to allow insertion and removal of an interior probe of the inspection device, magnetic coupling occurs through the hat stringer, as shown in FIG. 4. With access to the interior, through transmission ultrasonic (TTU) inspection techniques may be used.

In FIG. 3, probe 40 rides along a surface 14 of the skin 12. Probe 30 rides along the outer surface 16 of the hat stringer 10 and a surface 15 of the skin 12. A probe which rides inside a hat stringer may be magnetically coupled to a probe which rides on the outside of the hat stringer. Each probe 30, 40 may include one or more magnetic coupling devices 42 such as magnets or ferromagnetic material inserts to provide a magnetic coupling between the two probes 30, 40 to hold the probes 30, 40 in alignment and to provide leader-follower motion in tandem. Magnetic coupling may be adjusted by changing the size and/or strength of a magnet.

At least one probe may include inspection sensors such as a pulse echo sensor, ultrasonic transducer, x-ray source, x-ray detector, encoder, or camera. The ultrasonic transducer may be a 1 MHz immersion transducer from Agfa/Krautkramer of Lewistown, Pa. As shown in FIG. 3, one probe 30 includes ultrasonic transducers 36, 37, 38, 39 oriented to inspect various components of the hat stringer 10. Transducer 36 inspects a corner 24. Transducer 37 inspects a corner 26 that attaches to the skin 12. Transducers 38 inspect the side surface. Transducers 39 inspect the portion of the hat stringer 10 furthest from the skin 12.

The probes 30, 40 also include contact members 41 such as wheels, bearings, or skids to allow the probes 30, 40 to easily move across surfaces 14, 15 and 16. Each contact member 41 supports the probe 30, 40 at the proper spacing from the surface 14, 15 and 16 and reduces the frictional drag to permit smooth translation of the probe across the surface.

By magnetically coupling the probes 30, 40 to each other on opposing surfaces 14, 15 and 16 of the structure under inspection, either probe may be driven, i.e., moved across the respective surface of the structure under inspection by a translational force, thereby moving the opposing magnetically coupled probe. Each probe 30, 40 includes a housing 34, 44 to carry the various elements of the probe, such as the magnetic coupling devices 42, contact members 41, and inspection sensors 36, 37, 38, 39. The housing may be made, for example, from plexiglass, plastic, or other materials which provide structural support, durability, do not interfere with the inspection method, and are unlikely to damage the surface of the part under inspection such as by scratching the surface upon contact.

A probe 30 may be designed to accommodate hat stringers of different widths and hat stringers that vary in width. A probe 30 may be formed from two sides 46, 48. As the width of a hat stringer increases or when the inspection probe 30 is placed on a hat stringer with a large width, the probe 30 can separate into the first and second sides 46, 48. The first and second sides 46, 48 may be magnetically coupled to each other such as using magnetic coupling devices to support the first and second sides 46, 48 against the outside surface 16 of the hat stringer and prevent the first and second sides 46, 48 from separating more than the width of the hat stringer under inspection.

In FIG. 4, a probe 40 is located inside the hat stringer 10 and is supported against the inside surface 18 of the hat stringer 10.

Figure 5A:
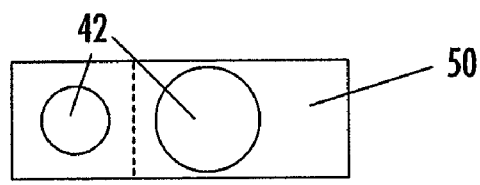
FIG. 5A is a bottom plan view of a portion of an inspection probe.
Figure 5B:
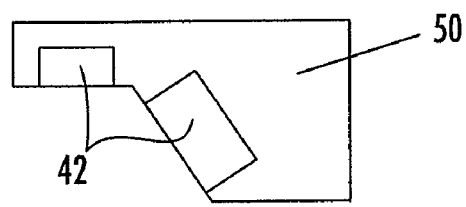
FIG. 5B is a cross-sectional schematic diagram of a portion of the probe of FIG. 5A.
Figure 6A:
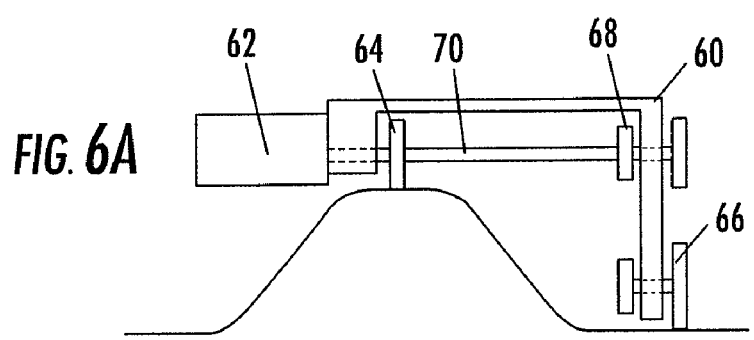
FIG. 6A is a cross-sectional schematic diagram of a portion of another inspection probe.
Figure 6B:
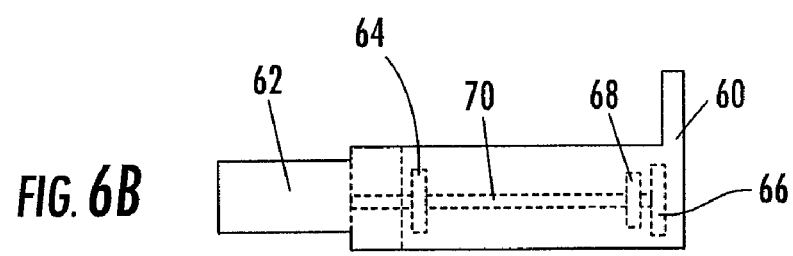
FIG. 6B is a cross-sectional schematic diagram of a portion of the probe of FIG. 6A.
Figure 6C:
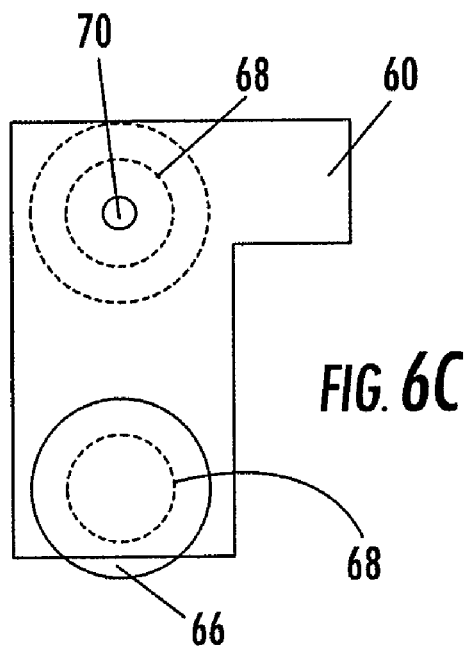
FIG. 6C is another cross-sectional schematic diagram of a portion of the probe of FIG. 6A.

FIG. 5A is a bottom plan view of a portion of an inspection probe; FIG. 5B is a cross-sectional schematic diagram of the portion of the probe of FIG. 5A. The probe 50 shown in FIGS. 5A and 5B includes magnetic coupling devices 42 to support the probe against a hat stringer and inspect a side and a top portion of the hat stringer. The probe may be attached to or integrally formed with the portion of a probe shown in FIGS. 6A, 6B, and 6C. The probe shown in FIGS. 6A, 6B, and 6C provides for movement along the length of a hat stringer for continuous inspection. The portion of an inspection probe shown in FIGS. 6A, 6B, and 6C may be referred to as a structural member, frame, body, or exoskeleton for supporting a probe. A housing 60 may support a motor 62 which drives an axle 70. The axle may turn one or more contact members 64 which support the housing 60 against a structure. The axle 70 may also support gears 68 which drive other contact members 66.

Figure 7:
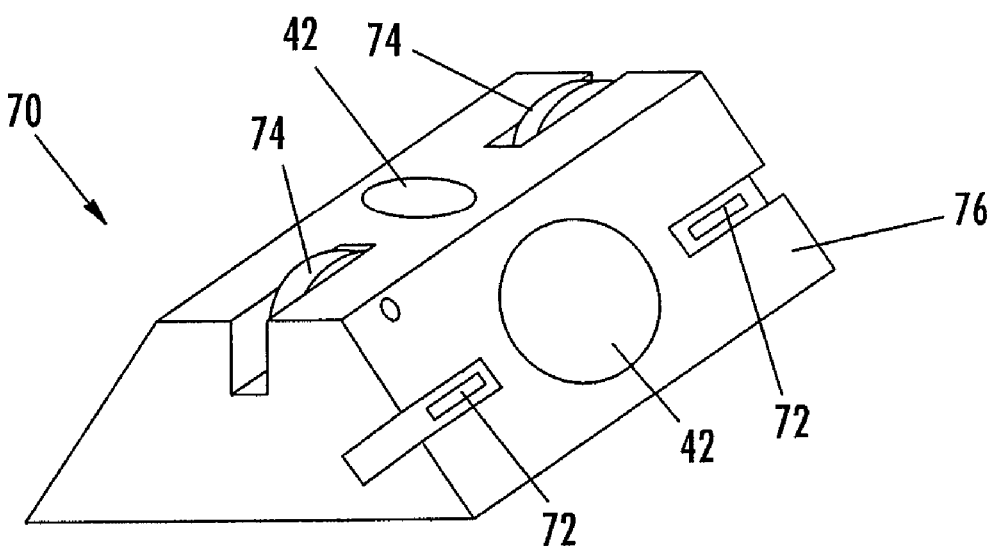
FIG. 7 is a perspective view of another inspection probe.

FIG. 7 is a perspective view of another inspection probe 70 that rides below or inside a hat stringer. The probe 70 includes contact members 72, 74, and magnetic coupling devices 42.

In FIGS. 8, 9, 10, 11, and 12, a probe 80 can inspect two surfaces of a hat stringer when moved in one direction and the remaining side when scanned in the opposite direction. Transducer holders 84 support and align the inspection sensors 38. Recesses 136, 138, 139 in the transducer holders 84 receive the inspection sensors and position the sensors to achieve complete scanning of hat stringer surfaces. Recess 139 is located to align a sensor to scan the top surface of a hat stringer. Recess 136 aligns a sensor to scan the corner or edge of the hat stringer. An end recess 138 positions a sensor to scan the side surface of the hat stringer.

Figure 11:
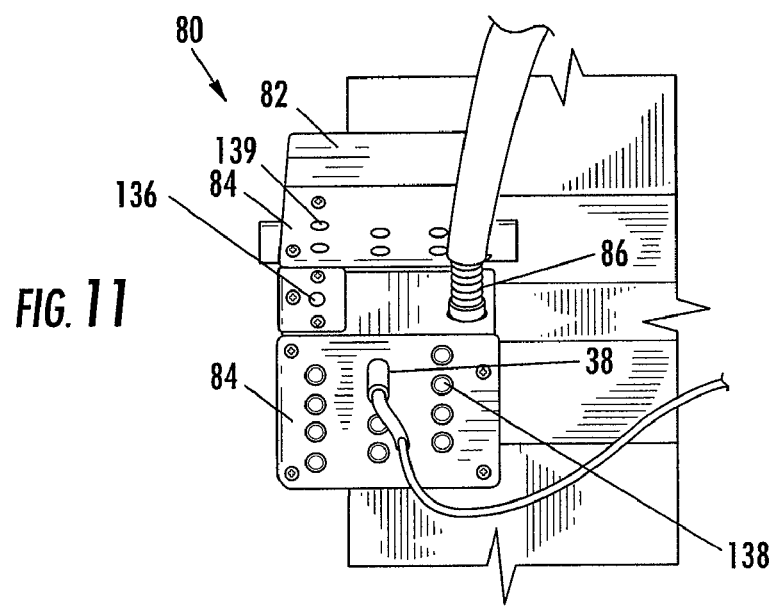
Figure 12:
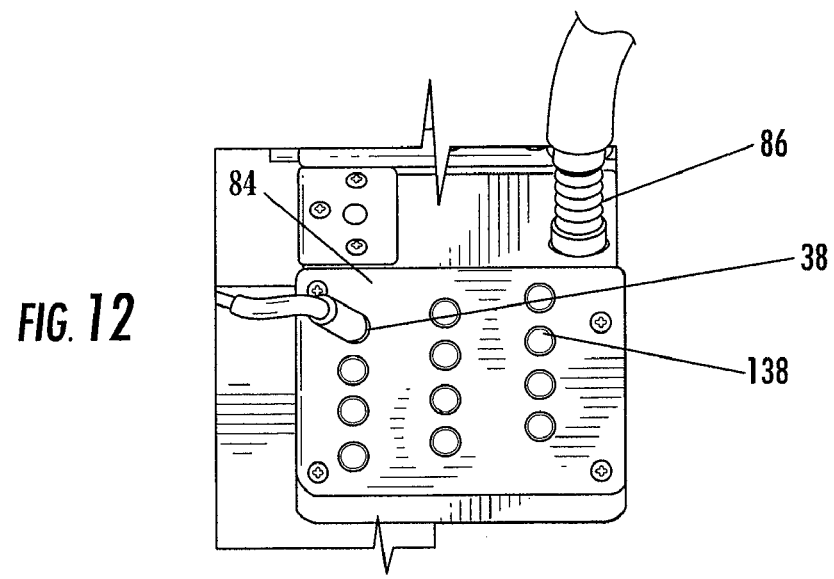

For ultrasonic inspection, a fluid, like water or air, can be fed through supply lines into channels on the inspection device to disperse the water between the device and the structure and to couple test signals between the inspection device and the structure. A fluid inlet 86 permits transfer of a fluid through the housing 82 to channels to disperse the fluid. The design of FIG. 8 maintains a fluid coupling path between inspection sensors 38 and the hat stringer when only a portion of the inspection probe 80 is over the hat stringer as shown in FIGS. 11 and 12. Advantageously, the fluid flows smoothly without bubbles, cavitation, or turbulence that would detrimentally affect the signal to noise ratio.

Also, instead of contact members, a fluid bearing may be created by pumping a thin layer of fluid, like water or air, between the housing and the surface of the structure. A fluid bearing may further prevent scratching of the surface.

Even if the probe has a fluid bearing, it may also include one or more contact members. Skids may be beneficial for fluid bearing probes to prevent damage or marring of a surface of a structure when initially placing a probe on the structure or magnetically coupling two probes on opposite sides of the structure, particularly when the fluid bearing is not be in use.

In FIG. 13, a probe 200 includes three separate transducer holders 202, 204, 206 which each include magnetic coupling devices 42 and recesses 138, 139 for inspection sensors. By separating each transducer holder 202, 204, 206, the probe 200 is capable of re-orienting each transducer holder 202, 204, 206 and any inspection sensors supported thereby as may be required for inspecting hat stringers with different shapes, different angles along the sides of the hat stringer, and/or different heights of the hat stringer. The probe 200 is used with a probe 90 as shown in FIG. 14. Probe 90 includes hinges 92, or other rotatable mechanics, that permit the side portions 93, 94 of the second inspection probe 90 to rotate to match the corresponding angle of the sides of the hat stringer. As such, the magnetic attraction between the magnetic coupling devices 42 of the first and second probes 200, 90 permit re-orientation of the side transducer holders 202, 204 to match the corresponding angle of the sides of the hat stringer. Accordingly, the side transducer holders 202, 204 of the first inspection on probe 200 match the angle of the outer surface 16 of the hat stringer 10 and the side portions 93, 94 of the second inspection probe 90 match the angle of the inner surface 18 of the hat stringer 10.

FIGS. 15, 16, and 17 show views of yet another inspection probe of the present invention. The embodiment of the inspection probe shown in these figures is akin to the portion of an inspection probe shown in FIGS. 6A, 6B, and 6C such that the housing 260 of the first inspection probe 210 is decoupled from the transducer holders or inspection shoes 202, 204, 206 of the first inspection probe 210. The housing, or exoskeleton, 260 of the first inspection probe 210 supports various components for the first inspection probe 210 to provide for support, alignment, and translation of the first inspection probe 210 along the length of a hat stringer for continuous inspection. A motor 262 is used to drive contact members 266 such as friction wheels. Gears 268 may be used to transfer the rotation of the motor 262 to the contact members 266 using a drive chain 269 or like translational means and an axle 270 for gear transmission. The first inspection probe may also include a linear encoder 261 such as an optical shaft encoder, a linear encoder, an optical sensor, a directional sensor, or wheel encoder that may be mounted to the housing 260 of the first inspection probe 210 to provide feedback of the position, speed, direction, and/or velocity of the first inspection probe 210. Embodiments of the present invention may use a smart stepper motor that drives the wheels and an optical encoder to denote location and speed of the inspection device. For example, an inspection device may be capable of inspecting at a rate as much as or more than ten feet in length of a hat stringer per minute, and a smart stepper motor can operate with an electronic controller, such as an a computer with control software, to move the inspection device in a manner advantageous to the speed of the scanning technology in use.

The first inspection probe 210 may cooperate with a second inspection probe 211 as seen in FIG. 17. Transducer holders, or shoes, 202, 204, 206 of the first inspection probe 210 may include magnetic coupling devices 42 which correspond with magnetic coupling devices 42 of the second inspection probe 211. The magnetic attraction between the corresponding magnetic coupling devices 42 of the first and second inspection probes 210, 211 provides for support and orientation of the transducer holders 202, 204, 206 along the outside surface of the hat stringer. The second inspection probe 211 and the transducer holders 202, 204, 206 may include contact members 41. To maintain proper alignment of the transducer holders 202, 204, 206, decoupling supports are used to adjust the alignment or orientation of the transducer holders 202, 204, 206. Probe 210 includes springs 213 and a vertical adjustment drive 212.

Probe 210 straddles the hat stringer to permit movement of the first probe 210 along the length of the hat stringer for inspection. Probe 211 is inside the hat stringer in the application of FIG. 17. Magnetic coupling devices 42 in the first and second probes 210, 211 provide magnetic attraction between the probes 210, 211 to maintain contact with opposing surfaces of the structure and corresponding relational positions with respect to the other probe, including during cooperative movement of the probes 210, 211. Contact members 41 of the probes 210, 211 permit controlled movement of the probes 210, 211 over the respective surfaces of the structure for inspection of the hat stringer. Inspection sensors, such as ultrasonic transducers, are activated to inspect the hat stringer as the probes 210, 211 are moved along the length of the hat stringer by the motor 262. Alternatively, movement of the probes may be provided by an automated control system or by manual operation. A couplant may be used to improve the quality of the inspection of the hat stringer.

As the inspection device moves along the length of the hat stringer, the probes 210, 211 may re-orient the magnetic coupling devices 42 and/or inspection sensors to the shape of the hat stringer such as to compensate for a change in the angle of the sides of the hat stringer.

In FIGS. 18, 19, 20, 21 and 22, probe 300 includes adjustable magnetic coupling devices 342 at either end. The magnetic coupling device 342 can adjust using a slidable portion 302 which can account for different heights of hat stringers. As more clearly visible in FIGS. 21 and 22, the inspection probe 300 includes two transducer holders 304, 306. One of the transducer holders 304 is configured to provide for positioning and alignment for scanning a side surface of a hat stringer. The other transducer holder 306 is positioned to provide alignment for scanning the top surface of a hat stringer. Corresponding recesses 338, 339 permit an array of inspection sensors to be located on each of these transducer holders 304, 306. The inspection probe 300 is configured to decouple the transducer holders 304, 306 from the housing 360 to permit the transducer holders 304, 306 and inspection sensors to reorient with respect to the surface being scanned. For example, the transducer holder 304 configured to scan the side of a hat stringer is attached to a support element 314 which is attached to the housing 360 with spring-biased dampers 318 which permit the support element 314 to achieve, to a certain extent, three degrees of freedom with respect to the housing 360. Spring-biased dampers 318 may be linear slides having linear rods with bearings to provide for movement toward and away from the surface of the hat stringer in addition to angular freedom of motion for aligning to the surface of the hat stringer. The transducer holder 304 is attached to the support element 314 by a hinged attachment 315 which permits an additional degree of freedom. The transducer holders 304, 306 have magnetic coupling devices that couple the transducer holders 304, 306 to the surface of the hat stringer by attraction to magnetic coupling devices of the probe inside the hat stringer. In FIGS. 23A-H, airpots or dashpots 312, 313 are included to dampen vibrations and/or oscillations which may deteriorate the inspection quality from the inspection sensors located on the decoupled transducer holders 304, 306.

In FIGS. 24, 25 and 26, a probe 400 is separated into first and second sides 402, 404 to permit the inspection probe 400 to achieve various widths. Magnetic coupling devices 442 provide magnetic attraction of probe 400 to support probe 400 against the surface of the hat stringer.

In FIGS. 27, 28, 29, 30, 31A, 31B, and 32A-E, a probe 500 includes a motor 462 surrounded by a motor housing 463 which drives the probe 500 along the surface of the structure under inspection to provide continuous scanning. For example, the motor may drive contact members such as wheels 466 which drive a tread 440 that rides along the surface of the skin. The motor 462 may translate its rotational force from a gear 468 to the contact members using a drive chain 469 such as a belt or chain. Configurations of inspection sensors may include arrays positioned on the inspection probe 500 to scan the entire surface of a hat stringer.

The invention should not be limited to the specific disclosed embodiments. Specific terms are used in a generic and descriptive sense only and not for purposes of limitation.

That which is claimed:

1. A probe for inspecting a structure comprising:
   a housing configured for traveling over a first surface of the structure under inspection, and wherein the housing is further configured to span a cross-section of a portion of the structure that protrudes from the first surface of the structure wherein the portion of the structure that protrudes from the first surface of the structure forms a hat stringer, and wherein the housing is further configured to span a cross-section of the hat stringer; and
   at least one inspection sensor carried by the housing for inspecting the structure as the probe is moved over the first surface of the structure.

2. The probe of claim 1, wherein the hat stringer comprises a top surface and two sides with a first corner and a second corner, respectively, between the top surface and the two sides, and wherein the probe comprises at least one inspection sensor oriented to inspect the first corner of the hat stringer.

3. The probe of claim 2, wherein the probe further comprises at least one inspection sensor oriented to inspect the second corner of the hat stringer adjacent to the first corner.

4. The probe of claim 3, wherein the hat stringer comprises a first edge and a second edge, respectively between the two sides and the first surface, wherein the first edge is adjacent the first corner and the second edge is adjacent the second corner, and wherein the probe further comprises at least one inspection sensor oriented to inspect the first edge.

5. The probe of claim 4, wherein the probe further comprises at least one inspection sensor oriented to inspect the second edge.

6. The probe of claim 1, wherein the at least one inspection sensor of the probe comprises an array of inspection sensors.

7. The probe of claim 6, wherein the probe further comprise at least one transducer holder connected to the housing and for supporting and orienting the array of inspection sensors.

8. The probe of claim 7, wherein at least one transducer holder is adjustably connected to the housing with spring-biased positional adjustment.

9. The probe of claim 1, wherein the probe is separated into a first side and a second side, and wherein each of the first side of the probe and the second side of the probe comprise at least one inspection sensor.

10. The probe of claim 9, wherein each of the first and second sides of the probe comprises at least one magnetic coupling device positioned to be magnetically coupled with a corresponding magnetic coupling device of the second side and the first side, respectively, thereby holding the first and second sides against the first surface of the structure.

11. The probe of claim 1, wherein the probe further comprises a motor connected to the housing and for moving the probe over the first surface of the structure.

12. The probe of claim 1, wherein the probe further comprises at least one magnetic coupling deyice carried by the housing.

13. The probe of claim 1, wherein the probe further comprises at least one contact member for supporting the probe on the structure as the probe is moved over the first surface of the structure.

14. The probe of claim 13, wherein the hat stringer comprises a top surface and two sides, and wherein the probe comprises at least one contact member oriented to support the probe on one of the sides of the hat stringer as the probe is moved over the first surface of the structure.

15. The probe of claim 13, wherein the contact members are selected from the group consisting a wheel, a ball bearing, a fluid bearing, a skid, and a tread.

16. The probe of claim 1, wherein the probe is separated into a first side and a second side, and wherein each of the first and second sides comprises at least one contact member for supporting the respective first and second sides of the probe on the structure as the probe is moved over the first surface of the structure.

17. The probe of claim 1, wherein the hat stringer comprises a top surface and two sides with a first corner and a second corner, respectively, between the top surface and the two sides, wherein the housing comprises a first side portion configured for traveling over a first side of the two sides of the hat stringer and connected along a first edge with a top portion configured for traveling over the top surface of the hat stringer and a second side portion configured for traveling over the second side of the hat stringer and connected along a second edge with the top portion, and wherein at least the first edge is adjustable to provide a rotatable connection between the first side portion of the housing and the top portion of the housing to permit the first side portion of the housing and the top portion of the housing to adjustably rotate to a corresponding angular orientation between the first side and the top portion of the hat stringer.

18. The probe of claim 17, wherein the first edge comprises at least one hinge.

19. The probe of claim 1, further comprising a linear encoder coupled to the housing and adapted to detect linear movement of the probe as the probe is moved over the first surface of the structure.

20. A probe for inspecting a structure comprising:

a housing configured for traveling over a first surface of the structure under inspection, and wherein the housing is further configured to span a cross-section of a portion of the structure that protrudes from the first surface of the structure wherein the portion of the structure that protrudes from the first surface of the structure forms a shape selected from the group of: a trapezoid, and a triangle, wherein the housing is further configured to span a cross-section of the shape, and wherein the housing comprises at least one angled portion corresponding to an angled surface of the shape and configured for riding along the angled surface of the shape as the housing travels over the first surface of the structure under inspection; and at least one inspection sensor carried by the housing for inspecting the structure as the probe is moved over the first surface of the structure.

* * * * *